United States Patent [19]

Stein et al.

[11] Patent Number: 4,886,164

[45] Date of Patent: Dec. 12, 1989

[54] CONTAINERS FOR MEDICAL WASTE

[75] Inventors: Israel M. Stein, Chestnut Hill; Alan S. Goodman, Roxbury; Richard Romanow, South Boston, all of Mass.

[73] Assignee: Enviro Med, Inc., Boston, Mass.

[21] Appl. No.: 367,173

[22] Filed: Jun. 16, 1989

[51] Int. Cl.4 .......................... B65D 5/12; B65D 81/00
[52] U.S. Cl. ..................................... 206/366; 229/907; 229/125.21; 229/131; 220/1 T; 220/403
[58] Field of Search .................... 206/366; 229/125.21, 229/125.28, 125.29, 907, 131; 220/404, 403, 1 T

[56] References Cited

U.S. PATENT DOCUMENTS

| | | |
|---|---|---|
| 1,603,024 | 10/1926 | Childs . |
| 3,012,660 | 12/1961 | Shelbon ........................ 229/125.21 |
| 3,226,007 | 12/1965 | Thies et al. . |
| 3,381,814 | 5/1968 | Benfield . |
| 4,121,755 | 10/1978 | Meseke et al. . |
| 4,315,592 | 2/1982 | Smith . |
| 4,373,629 | 2/1983 | Ulin et al. . |
| 4,410,086 | 10/1983 | Simpson . |
| 4,452,358 | 6/1984 | Simpson . |
| 4,454,944 | 6/1984 | Shillington et al. . |
| 4,466,538 | 8/1984 | Gianni . |
| 4,488,643 | 12/1984 | Pepper . |
| 4,494,652 | 1/1985 | Nelson et al. . |
| 4,520,926 | 6/1985 | Nelson . |
| 4,534,489 | 8/1985 | Bartlett . |
| 4,576,281 | 3/1986 | Karksey . |
| 4,580,688 | 4/1986 | Harris et al. . |
| 4,600,112 | 6/1986 | Shillington et al. . |
| 4,657,176 | 4/1987 | Matsubara ...................... 229/125.21 |
| 4,662,516 | 5/1987 | Baker et al. . |
| 4,674,676 | 6/1987 | Sandal et al. . |
| 4,714,168 | 12/1987 | Johnson et al. . |
| 4,715,498 | 12/1987 | Hanifl . |
| 4,736,844 | 4/1988 | Scott et al. . |
| 4,779,728 | 10/1988 | Hanifl et al. . |
| 4,804,090 | 2/1989 | Schuh et al. . |
| 4,809,850 | 3/1989 | Liable et al. . |

FOREIGN PATENT DOCUMENTS

| | | | |
|---|---|---|---|
| 324383 | 1/1930 | United Kingdom | ........... 229/125.21 |
| 2198120 | 6/1988 | United Kingdom | ............... 229/131 |

OTHER PUBLICATIONS

Federal Register, vol. 54, No. 56, Mar. 24, 1989, pp. 12374 & 12375.

Primary Examiner—Stephen Marcus
Assistant Examiner—Jacob Ackun, Jr.
Attorney, Agent, or Firm—Martin LuKacher

[57] ABSTRACT

Containers suitable for storage and transport of regulated medical waste, including sharps and solid and semi-solid waste, which is disposable with the waste as by incineration, are provided by low cost paper, preferably corrugated paper, boxes having inserts which provide a mouth through which the waste items may be inserted. The insert has side walls which are attached to the side walls of the box near the top thereof. The insert has notches in the side walls along its bottom. A cover panel having tabs with spacing complimentary to the spacing of the notches is placed in the box upon the bottom of the insert with the tabs in the notches. The box may be lined with a plastic bag to provide leak resistance. The bag extends between the side walls of the insert and the side walls of the box and above the top of the box. The cover may also have a sleeve of flexible plastic material. To close the container, the plastic bag is tucked in so that it lies above the bottom of the insert. When the cover panel is placed in the insert, a seal is formed. Because of the notches, the insert is difficult to remove and any tampering becomes visible because of damage to the notches or tabs. For large solid or semi-solid waste items, the insert mouth is provided by providing a closure flap with part of the insert. A fold across the bottom of the insert and slits in the side walls extend upwardly, the entire height of the side walls at opposite ends of the fold. The side walls on one side of the slits are connected, as by stapling to the side walls of the box. Then the other side of the insert is pivotal providing the flap.

22 Claims, 5 Drawing Sheets

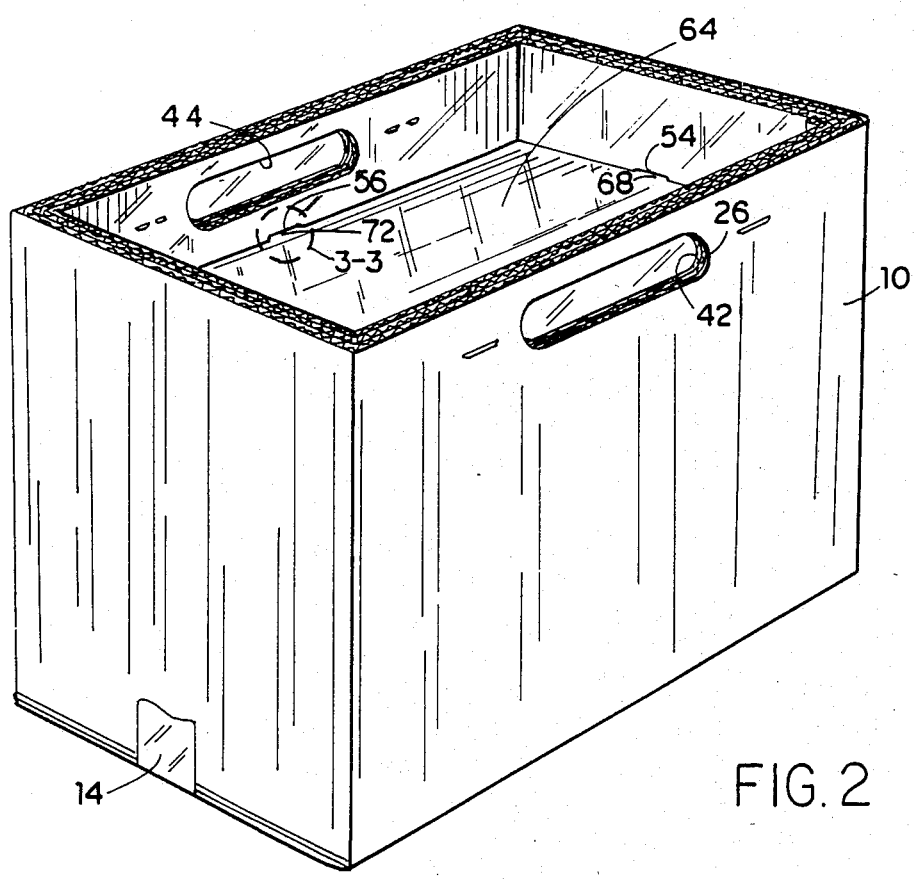
FIG. 2
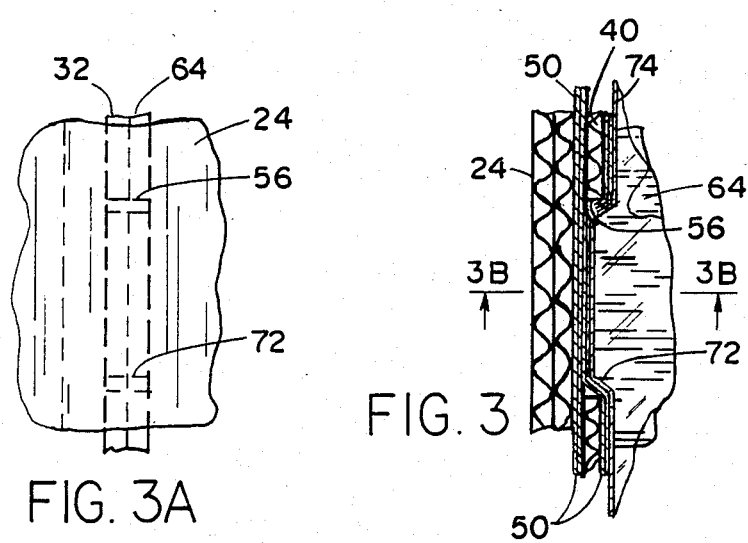
FIG. 3A
FIG. 3

CONTAINERS FOR MEDICAL WASTE

DESCRIPTION

The present invention relates to containers which are suitable for regulated medical waste generated in physicians' offices, hospitals and at other locations and for transport of the waste to a disposal site such as an incinerator.

The invention is useful for both sharps (hypodermic needles, syringes, scalpel blades, blood vials, culture dishes and broken or unbroken glass ware) as well as for items of dry or semi-solid waste which may be infectious such as gauze pads, gloves, gowns, blood soaked linen, blood tubes, etc.

Generators of medical waste are subject to regulations upon the storage of medical waste on site (in their offices, laboratories and clinics). Transporters who pick up medical waste and deliver them to treatment or destruction facilities such as incinerators are also subject to regulation. The regulations specify the requirements for containers which store medical waste. The latest regulations are set forth in 40 CFR §259 and packaging requirements are specifically set forth in §259.41. See Federal Register, Vol. 54, No. 56 for Friday, Mar. 24, 1989 at page 12374. In accordance with these requirements containers should be sealed to prevent leakage during transport with tight lids or stoppers. There are other practical requirements, particularly for sharps containers which are to make it difficult or impossible to remove the sharps items once they are placed in the container.

Many items of medical waste, particularly infectious waste, may quickly become malodorous. It is therefore necessary to enable containers for such waste to be temporarily closed between insertion of items and yet enable permanent locking and sealing of the containers when they are ready to be transported to the disposal site. All of these requirements should be met in a container which is low in cost, since the container and the waste is disposed of, as by incineration, and is therefore used only once. A low cost container is socially desirable since the cost is then not a factor discouraging use; policing of tens of thousands of locations where medical waste is generated being difficult if not impossible.

Various container designs have been proposed and most existing containers are in the form of plastic boxes with snap over or snap down lids. Once snapped, the lids are locked in place and cannot be removed. The following U.S. patents show various types of plastic containers for medical waste: Pepper, 4,488,643, December, 1984; Nelson et al., 4,494,652, January, 1985; Nelson, 4,520,926, June, 1985; Shillington et al., 4,454,944, June, 1984; Karksey, 4,576,281, March, 1986; Harris et al., 4,580,688, April, 1986; Shillington et al., 4,600,112, June 15, 1986; Baker, et al., 4,662,516, May, 1987; Johnson, et al., 4,714,168, December, 1987; Hanifl, 4,715,498, December, 1987; Scott et al., 4,736,844, April 19, 1988; Hanifl et al., 4,779,728, October, 1988; Liable et al., 4,809,850, March, 1989; Schuh et al., 4,804,090, February, 1989; Benfield, 3,381,814, May, 1968; Ulin et al., 4,373,629, February, 1983; Gianni, 4,466,538, August, 1984. Some containers have been proposed which are made of paper and corrugated cardboard. However, they have been of special design requiring extensive retooling over and above that used in conventional cardboard containers and are not believed to be in extensive use. See the following U.S. patents. Childs, 1,603,024, October, 1926; Thies et al., 3,226,007, December, 1965; Meseke et al., 4,121,755, October, 1978; Smith, 4,315,592, February, 1982; Simpson, 4,410,086, Oct. 18, 1983; Simpson, 4,452,358, June, 1984; Bartlett, 4,534,489, August, 1985 and Sandal et al., 4,674,676, June, 1987.

Accordingly, it is the principal object of the present invention to provide improved containers for medical waste.

It is another object of the present invention to provide improved containers for storage of regulated medical waste prior to transport in locations where the waste is generated as well as during transport to sites where the waste is treated or destroyed and which is suitable for sharps and for larger items of dry and semi-solid waste, different containers being provided in accordance with the invention for these separate purposes.

It is a further object of the present invention to provide improved containers for medical waste which may be made available at lower cost than containers for this purpose which are presently available.

It is a still further object of the present invention to provide improved, low cost containers for medical waste which are adapted to be sealed and locked, which sealing and locking is of the nature to discourage tampering and to make tampering apparent.

It is a still further object of the present invention to provide improved containers for medical wastes which may be malodorous which are adopted to be temporarily sealed so as to counteract the escape of malefactory odors and which nevertheless can be provided at low cost. It is a still further object of the inventors to provide improved low cost containers for medical waste which can readily be provided handles for ease of loading and unloading from a transport vehicle and are located away from the regions of the containers in which the waste is disposed thereby avoiding potential hazards when lifting and carrying the containers.

Briefly described, a container for medical waste in accordance with the invention utilizes a box which may be made of corrugated paper and may be of conventional design The box has a bottom and side walls. It is open at the top and does not have the conventional top flaps. An insert also having a bottom and side walls which is complimentary in shape to the side walls of the box is attached at the top of the box with the bottom of the insert below the top of the box. A plastic (e.g. polyethylene) liner bag or bags may be disposed in the box with the sides of the bag extending between the side walls of the box and the insert and above the top of the box. The bottom of the insert has a mouth, which in the case of a sharps container is a narrow slot which enables the sharps items to be placed into the box, but discourages placing of larger items which might force the needles and other sharps through the liner or even through the walls of the box. Closing, sealing and locking is facilitated by providing the plurality of notches in the side walls of the insert where the side walls meet the bottom of the insert. A cover panel which may be contained in a sleeve of plastic has tabs along its edges with the same spacing as the notches in the side walls of the insert. This cover panel is pushed down into the top of the box and closes and locks the box; the plastic material of the bag being first tucked in and over the bottom of the insert such that when the cover is in place, a plastic to plastic seal automatically forms. The closure and locking requirements of the government regulations are then met. Moreover, the tabs do not extend through the side walls of the box. It is therefore very difficult to remove the cover. This discourages tampering. Moreover, any tampering damages the tabs and notches and is readily detected.

Containers for larger items of solid and semi-solid waste may be larger than the containers for sharps. In order to provide for temporary sealing of such containers, the insert has a fold, preferably about two-thirds the distance between its opposite ends. The side walls at opposite ends of the inserts are slit so that the larger part of the insert is pivotal as a flap between closed position and an open position (preferably when pivoted upwardly towards the top of the box) to provide a mouth for the insertion of the items of medical waste. The smaller part of the insert in attached at its side walls to the side walls of the box. When the container is closed, the pivotal part of the insert is also attached, as by stapling of the side walls thereof to the side walls of the box. Plastic liners may be provided which are tucked in and the box is sealed with a cover panel as in the case of the sharps container described above.

The foregoing and other objects, features and advantages of the invention, as well as presently preferred embodiments thereof, will become more apparent from a reading of the following description in connection with the accompanying drawings in which:

FIG. 2 is a perspective view showing the container of FIG. 1 in closed, locked and sealed condition;

FIG. 3 is a fragmentary sectional plan view of the area indicated at 3—3 in FIG. 2;

FIG. 3A is an end view of FIG. 3;

Figure 1:
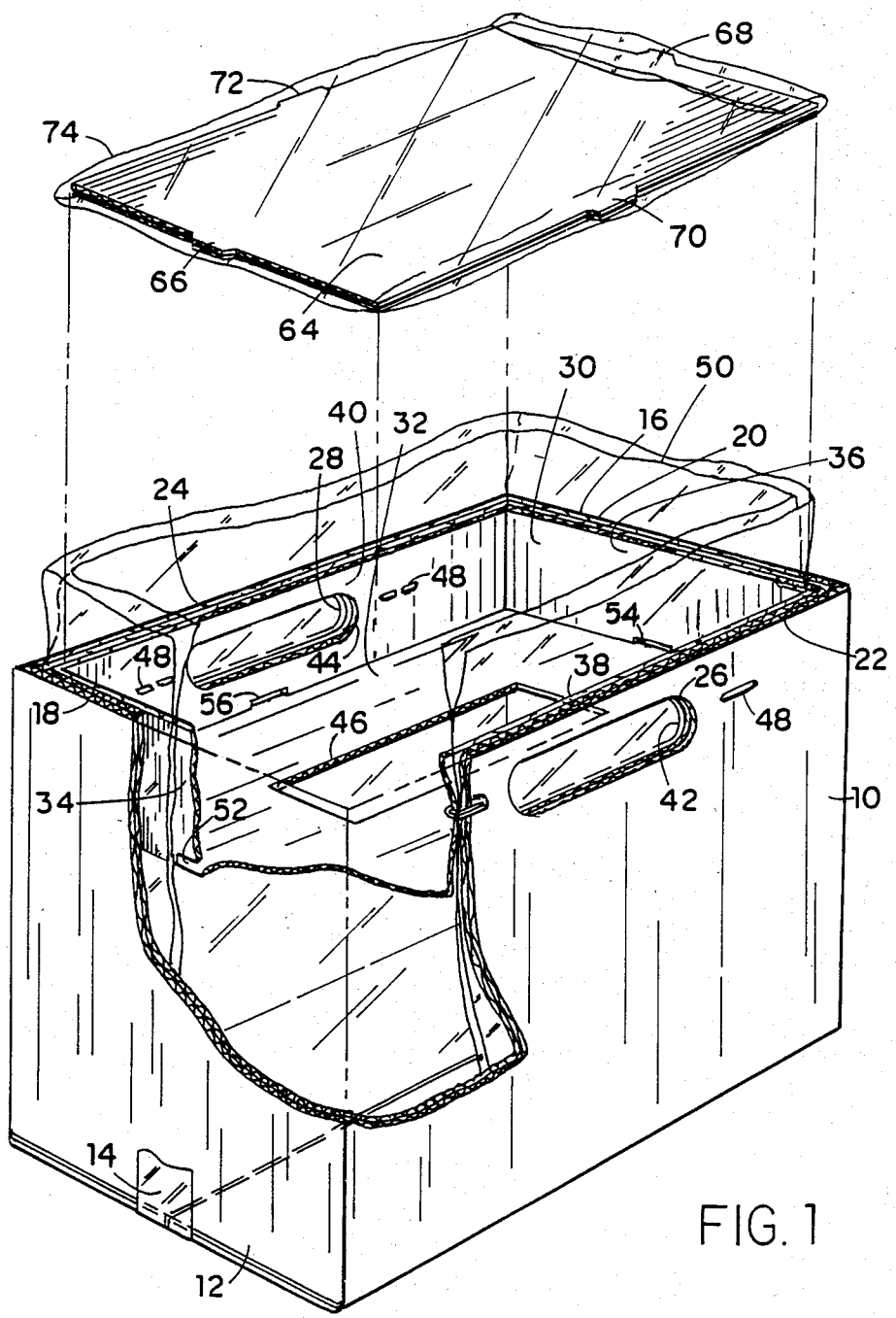
FIG. 1 is a perspective, partially broken away view of a container which is especially adopted for sharps medical waste, the cover of the container being shown spaced from the remainder of the container in exploded view.

Referring to FIGS. 1, 2, 3, 3A and B there is shown an exemplary sharps container embodying the invention. The container may be relatively small approximately 12 inches by 8 inches by 9 inches high. A conventional box of double walled corrugated paper 10 is closed at the bottom 12 thereof by sealing tape 14. The top 16 of the box is open; the opening being defined by the top edges of side walls 18, 20 and 22, 24 of the box 10. These side walls are corrugated panels having folds. They may be stored flat and assembled into the rectangular box in the conventional way. The larger side walls 22 and 24 have slots 26 and 28 which provide handles for the container.

Disposed inside the container is an insert 30 also made of corrugated paper which may be single walled. This insert has a bottom 32 and opposite side walls 34, 36 and 38, 40. These side walls may be flaps extending from folds along the edges of the bottom 32. The larger side wall flaps 38 and 40 have slots 42 and 44 which are aligned with the slots 26 and 28 in the side walls 22 and 24 of the box 10 to define the handles for the container. It will be apparent as the description proceeds that these handles are very easy to make (requiring only alignable slots) and are located well above the waste containing part of the container, which is recessed below the handles. Potential hazards in lifting and carrying the container, as upon loading and unloading from the transport vehicle, are avoided.

The insert has a long narrow slot 46 along the medial portion thereof which provides a mouth for the insertion of the sharps items. The side walls 34, 36 and 38, 40 of the insert are attached to the side walls of the box as by staples 48, a few of which are shown. The size and shape of the insert and the shape of the box adjacent to the top thereof are complimentary so that the insert fits tightly into the box. The upper edges of the side walls 34, 36 and 38, 40 of the insert are in alignment with the top edges of the side walls of the box. The bottom 32 of the insert is depressed, for example two or three inches below the top edges.

A bag 50 and in this exemplary embodiment, two bags which are interfitted in each other and are of plastic, for example two to four mill polyethylene material, is disposed in and provides a liner in the box. The bags extend to the bottom of the box and provides leak resistance and makes the container impervious to moisture. The top of the bag 50 extends above the top edge of the box and side walls. The sides of the bag are sandwiched between the side walls of the insert 30 and the side walls of the box 10.

Figure 3B:
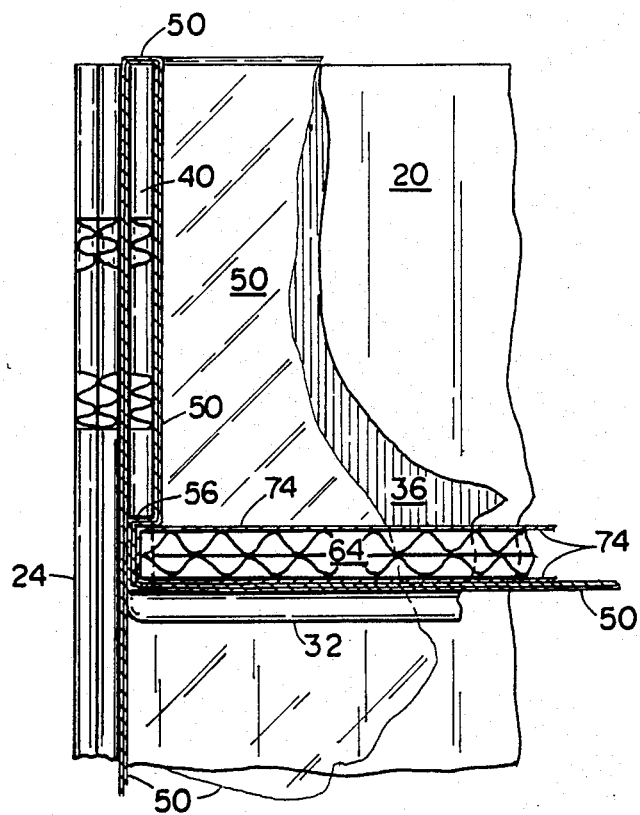
FIG. 3B is a sectional view along the line 3B—3B in FIG. 3.

As best shown in FIGS. 3, 3A and 3B there are a plurality of notches in the side walls of the insert 30 where the side walls meet the bottom 32 of the insert. There are opposed notches 52 and 54 in the side walls 34 and 36, and opposed notches 56 and 58 in the side walls 38 and 40 (see also FIG. 5). The notch 58 in the side walls 38 and 40 (see also FIG. 5). The notch 58 in the side wall 38 diametrically opposite from the notch 56 is not shown in FIGS. 1 & 2. A cover 64 is used to close, lock and seal the container 10. The cover 64 is a piece of single ply corrugated paper of the same size and shape as the bottom 32 of the insert 30. This cover is inserted in a sheath or sleeve 74 which may be of plastic flexible material (e.g. polyethylene film). The sleeve 74 is larger than the cover. The cover has opposed tabs 66, 68 and 70, 72 in opposite edges thereof. These tabs are spaced in the same relationship as the notches in the cover panel.

In order to seal, close and lock the container 10, the upper part of the bag 50 is tucked in and down upon the bottom 32 of the insert 30. Then the cover 64 is pressed down into the insert until the tabs 66, 68 70, 72 snap into the notches 52, 54, 56, 58. A seal is automatically formed between the plastic sheath 74 and the tucked in portion of the bag 50. Removal of the cover is difficult and tampering is readily detected since the notches will be distorted and the tabs 66, 68 and 70, 72 bent. The container then may readily be permanently locked and sealed when closed. It can be picked up by the handles formed by the aligned slots 26, 42 and 28, 44 and transported to the disposal site.

Figure 4:
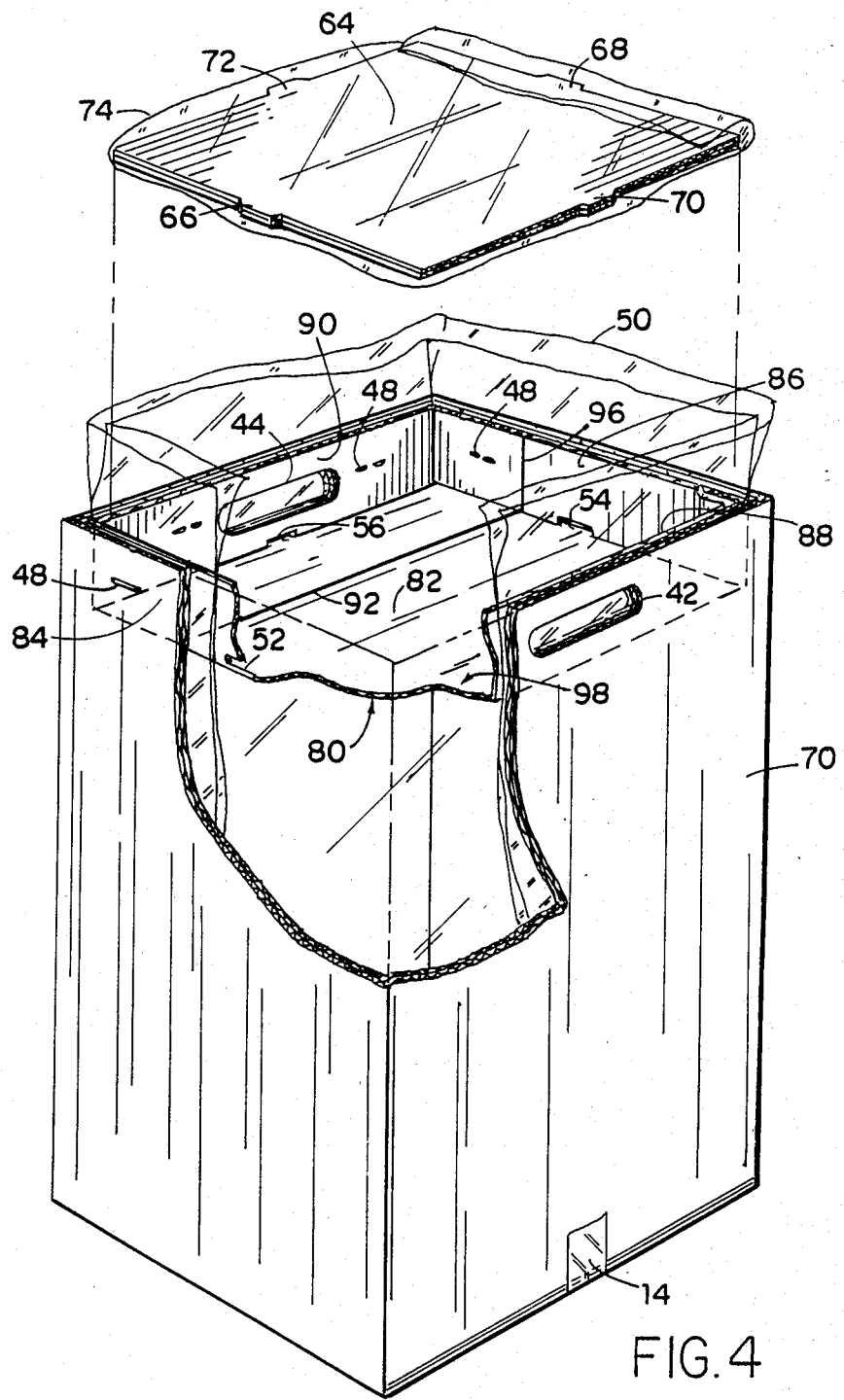
FIG. 4 is a view similar to FIG. 1 of a container for larger items of dry or semi-solid medical waste.
Figure 5:
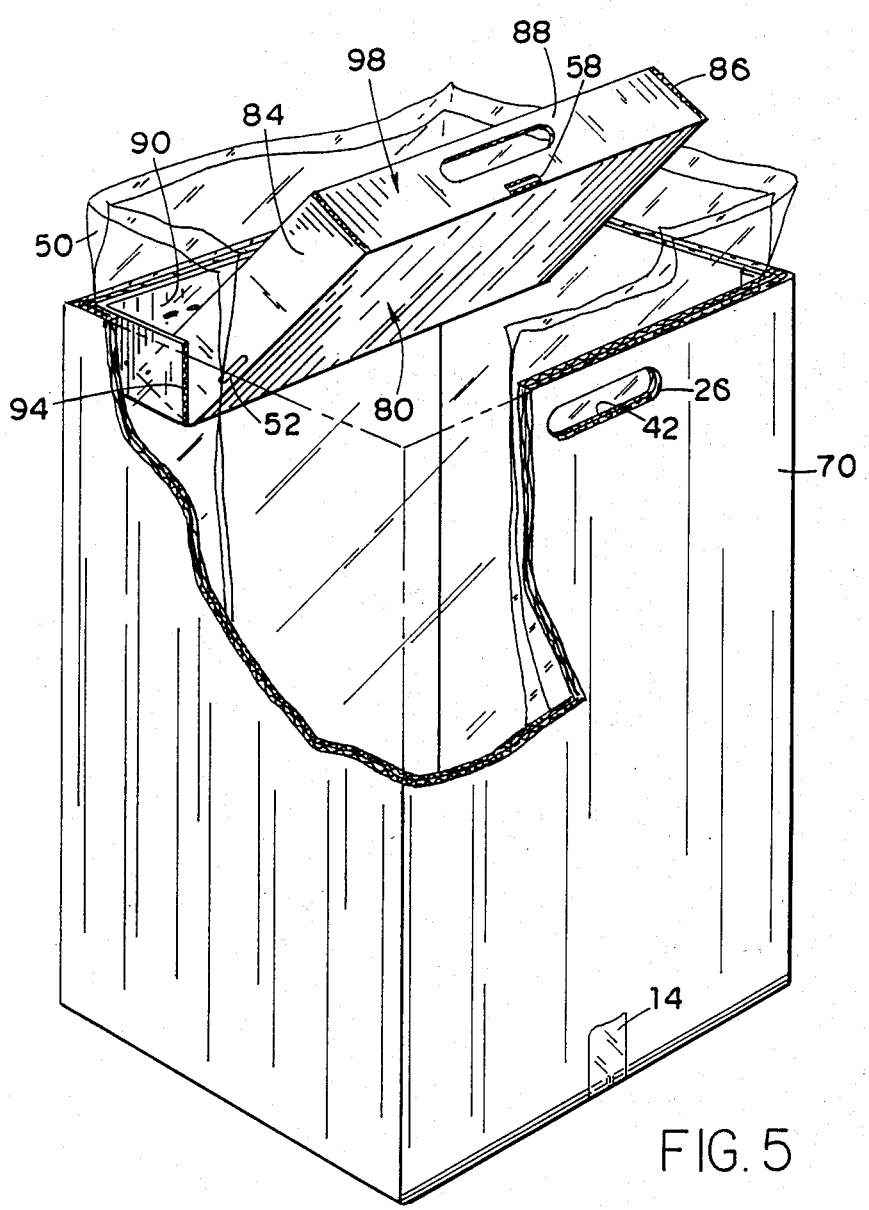
FIG. 5 is a perspective view of the container shown in FIG. 5, before the cover panel is in place, showing the insert pivoted upwardly as a flap to present a mouth for the insertion of items of medical waste into the box.

Referring to FIGS. 4 and 5 there is shown a container 70 for dry and semi-solid waste. This container is preferably higher than the sharps container 10 and may for example be approximately 30 inches high, 15 inches wide and 18 inches long. The container 70, like the sharps container 10, is a box which is preferably of double wall (e.g., 275 pounds strength) corrugated paper with an open top and closed bottom. An insert 80 which has a bottom 82 and side flaps 84, 86, 88 and 90 and is of the same size and shape as the box, is disposed in the box adjacent to the top end thereof. The top edges of the insert 80 are aligned with the top edges of the box 70. The insert also has notches which receives a cover when the container is sealed. These notches and cover are identified by the same referenced numerals as the cover 64 with its tabs 66, 68, 70, 72 and sleeve 74. Accordingly, like reference numerals are assigned to these like components of the container 70.

The insert 80 is characterize by a fold 92 which extends across the bottom 82 between the side walls 84 and 86. These side walls have slits 94 and 96 which extend from the fold upwardly to the top edges of the side walls. The fold and the slits are located preferably about one-third the distance from the side wall 90 and define a flap part 98 of the insert 80. The Part of the insert on the opposite side of the fold 92 and slits 94, 96. The smaller one-third of the insert is permanently attached as by the staples 48 to the side walls of the box.

To provide a mouth for the insertion of the items into the container, the flap part 98 need only be pivoted upwardly. To seal the container, the flap is pivoted downwardly and the side walls 88, 84 and 86 of the part 98 bear against the side walls of the container box 70 (via the sealing bag 50). This temporarily closes the container and prevents the escape of odors as well as placing the waste out of view.

When the container is full or otherwise is desired to be closed, the flap 98 is pushed down to close position and its side walls are stapled to the side walls of the container box 70. The bag 50 can then be tucked in and the cover panel 64 inserted to close, lock and seal the container 70.

From the foregoing description, it will be apparent that there has been provided improved containers for medical waste. Because the corrugated boxes which constitute the majority of the containers are essentially conventional and because only two additional parts are needed to provide a mouth and sealable covers, the containers can be provided at low cost. Variations and modifications in the herein described containers within the scope of the invention will undoubtedly suggest themselves to those skilled in the art. Accordingly, the foregoing description should be taken as illustrative and not in a limiting sense.

We claim:

1. A container for medical waste which comprises a box having a closed bottom and side walls extending upwardly to an open top, an insert having a bottom with side walls complimentary in shape to the side walls of said box in the region of said box which is adjacent to the top thereof, said insert being disposed within said box at the top thereof with said bottom of said insert spaced from said top, said bottom of said insert having a mouth for receiving items of medical waste, said side walls of said insert having a plurality of notches therein in spaced relationship with each other and disposed along said bottom of said insert where said side walls of said insert meets that bottom of said insert, and a cover panel having edges, tabs extending from said edges and disposed in the same spaced relationship as said notches, said cover panel being disposed on said bottom of said insert closing and locking said mouth with said tabs in said notches in order to close and lock said container.

2. The container in accordance with Claim 1 further comprising a liner bag of flexible material in said box and extending upwardly between the side walls of said box and the side walls of said insert above the top of said box, a sleeve of flexible material in which said cover is disposed, said bag being tucked into said box with said portions extending over the bottom of said insert and being sandwiched between said cover and the bottom of said insert to provide a seal between said cover and the bottom of said insert when said cover is disposed in said box to close and lock said container.

3. The container in accordance with Claim 2 wherein said mouth is a slot in and disposed along a medial portion of said bottom of said insert.

4. The container according to Claim 1 wherein said side walls of said box are attached to said side walls of said container so as to permanently locate said insert in said box.

5. The container in accordance with Claim 1 wherein said box is rectangular in cross section with opposed pairs of said side walls, said insert having a rectangular bottom with two pairs of opposed flaps defining the side walls of said insert, said flaps being attached to said side walls of said box, a first pair of said notches disposed in a first two of said four side wall flaps which are opposed to each other, a second pair of said notches being proposed in a second two of said side wall flaps which are also opposed to each other, said first pair of notches being opposite to each other and said second pair of notches being opposite to each other, said cover being rectangular with said edges being opposite edges thereof, said tabs being arranged in pairs which are diametrically opposite to each other and extend from said opposite edges.

6. The container in accordance with Claim 4 wherein said notches are disposed along medial portions of said first two and said second two of said side wall flaps, and said tabs are also disposed along medial portions of said opposite edges of said cover.

7. The container in accordance with Claim 4 wherein said box, said insert and said cover are of corrugated paper material.

8. The container in accordance with Claim 6 . wherein said corrugated material of said box is double walled.

9. The container in accordance with Claim 2 wherein said box is rectangular in cross section with opposed pairs of said side walls, said bottom of said insert being rectangular with opposed flaps defining four side walls of said insert, said flaps being attached to said side walls of said box with said liner bag therebetween, a first pair of said notches being disposed in a first two of said four flaps with are opposed to each other, a second pair of said notches being disposed in a second two of said flaps which are opposed to each other, said first pair of notches being opposite to each and said second pair of notches being opposite to each other, said cover being rectangular with said edges being opposite edges thereof. Said tabs being arranged in pairs which are diametrically opposite to each other and extend from said opposite edges, and said sleeve being longer in length and wider than said cover so as to fit into said notches when said tabs are inserted therein.

10. The container according to Claim 1 where in said insert has a fold across the bottom thereof, slits in said side walls of said insert at opposite ends of said bottom, said side walls of said insert being attached to the side walls of said box on one side of said slits, said bottom of said insert and said side walls on the opposite side of said slits being pivotal as a flap about said fold so as to provide said mouth when said insert is pivoted away from the side walls of said box.

11. The container in accordance with Claim 9 wherein said box and said insert are rectangular and said fold is approximately two-thirds of the distance. along said bottom to provide portions along about one-third and about two-thirds of said distance, said two-thirds portion providing said flap, and attachment means between the side walls of said box and the side walls of said insert in said one-third portion thereof.

12. The container according to Claim 9 wherein said side walls of said insert on the opposite side of said slits are also attached to the side walls of said box when said container is permanently closed, said cover being disposed on said bottom with said tabs in said notches when said side walls of said insert on the opposite side of said slits are attached to said side walls of said box.

13. The container according to Claim 9 further comprising a bag of flexible material lining said box and extending between the side walls of said box and said insert above the top of said box and tuckable into said box over the bottom of said insert when said container is to be closed so that said cover forms a seal with said bag when said cover is disposed with the tabs thereof in said notches upon the bottom of said insert.

14. A container for medical waste which comprises a box having a closed bottom, an open top and side walls extending from said bottom to said top and having edges defining the perimeter of said open top, an insert having a bottom and side walls of the same shape as said perimeter, said side walls of said insert having top edges, said bottom of said insert having a fold there across, slits in said side walls of said insert extending from said bottom to said top edges thereof to define first and second parts of said inserts on opposite sides of said fold and slits, said insert's side walls of said first part being attached to said box's side walls and said second part being pivotal as a flap between closed position and open position to provide a mouth for the insertion of items of medical waste, said side walls of said insert's second part bearing against said box's side walls to close said mouth and temporarily close said container.

15. The container according to Claim 13 wherein said side walls of said second part of said insert are attached to said box's side walls when said container is to be permanently closed.

16. The container according to Claim 12 further comprising a bag of flexible material lining said box and extending along the side walls thereof and between said side walls of said box and said side walls of said insert above the top of said box.

17. The container according to Claim 13 wherein said box and said insert are rectangular in shape, said insert bottom being rectangular with folds at opposite ends thereof to provide flaps defining defining said side walls of said insert and being rectangular panels.

18. The container according to Claim 16 wherein said box and said insert are made of corrugated paper.

19. The container according to Claim 16 where in said fold is about two-thirds the distance along an opposed pair of side edges which define the long side of said insert.

20. The container according to Claim 13 wherein said box and said inserts are provided by corrugated paper panels connected by folds at the intersections of the side walls of said box and at the intersection of said side walls of said box and the bottom of said box and at the intersection of said bottom of said insert and said side walls of said insert.

21. The container according to claim 1 further comprising handles on said box provided by slots the opposite side walls of said box and of said insert which slots are in alignment with each other.

22. The container according to claim 1 wherein said slots providing said handles are located about midway between said insert's bottom and the top of said box.

* * * * *